United States Patent
Bhise et al.

(10) Patent No.: US 12,383,491 B2
(45) Date of Patent: *Aug. 12, 2025

(54) READY-TO-USE INJECTABLE PHARMACEUTICAL COMPOSITIONS COMPRISING NEOSTIGMINE AND GLYCOPYRROLATE

(71) Applicant: AZURITY PHARMACEUTICALS, INC., Woburn, MA (US)

(72) Inventors: Rahul Dhulaji Bhise, Hyderabad (IN); Ajay Kumar Singh, Princeton, NJ (US); Mahadeo Vasant Mahadik, Hyderabad (IN); Ashish Anilrao Dubewar, Hyderabad (IN); Molugu Prashanth Reddy, Hyderabad (IN)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 920 days.

This patent is subject to a terminal disclaimer.

(21) Appl. No.: 17/386,139

(22) Filed: Jul. 27, 2021

(65) Prior Publication Data
US 2021/0369604 A1    Dec. 2, 2021

Related U.S. Application Data

(63) Continuation of application No. 16/170,948, filed on Oct. 25, 2018, now Pat. No. 11,110,054.

(30) Foreign Application Priority Data

May 9, 2018   (IN) .............................. 201841017552

(51) Int. Cl.
| | | |
|---|---|---|
| *A61K 31/555* | (2006.01) | |
| *A61K 9/00* | (2006.01) | |
| *A61K 9/08* | (2006.01) | |
| *A61K 9/19* | (2006.01) | |
| *A61K 31/27* | (2006.01) | |
| *A61K 31/40* | (2006.01) | |
| *A61K 47/18* | (2017.01) | |

(52) U.S. Cl.
CPC .............. *A61K 9/0019* (2013.01); *A61K 9/08* (2013.01); *A61K 31/27* (2013.01); *A61K 31/40* (2013.01); *A61K 47/183* (2013.01)

(58) Field of Classification Search
CPC ...... A61K 31/27; A61K 31/40; A61K 47/183; A61K 9/0019; A61K 9/08; G01J 1/0228; G01J 1/42; G01J 2001/4238; G01J 2001/4466; G01S 17/10; G01S 17/894; G01S 7/4865; G01S 7/497
See application file for complete search history.

(56) References Cited

U.S. PATENT DOCUMENTS 7,915,229 B2    3/2011    Cohen et al.

FOREIGN PATENT DOCUMENTS

| CN | 104288143 A | 1/2015 |
|---|---|---|
| IN | 2783MUM2012 | 9/2012 |
| WO | WO 01/08681 A1 | 2/2001 |

OTHER PUBLICATIONS

Bloxiverz, product label, FDA, May 2013 (Year: 2013).*
Robinul, Product Label, NDA 17-558/S-053, Jul. 5, 2016 by Wayback machine (Year: 2016).*
McIntyre et al (Trends in Cardiovascular Medicine 27 (2017) 506-513) (Year: 2017).*
Dailymed Label: Neostigmine Methylsulfate—neostigmine methylsulfate injection, solution. Fresenius Kabi USA, LLC. 17 pages, revised Nov. 2018.
Mercury Pharma: Glycopyrronium Bromide 0.5mg and Neostigmine Metilsulfate 2.5mg in 1ml solution for Injection. 5 pages, Nov. 11, 2017.
Mirakhur et al., "Glycopyrrolate-Neostigmine Mixture for Antagonism of Neuromuscular Block: Comparison with Atropine-Neostigmine Mixture", Br. J. Anaesth., vol. 49, p. 825-829, (1977).
Walker, M.B. Proceedings of the Royal Society of Medicine, 1935, vol. xxviii, No. 448, pp. 33-35.

* cited by examiner

*Primary Examiner* — Jean P Cornet
(74) *Attorney, Agent, or Firm* — Birch, Stewart, Kolasch & Birch, LLP

(57) ABSTRACT

Stable, ready-to-use injectable pharmaceutical compositions are provided, comprising the combination of neostigmine, glycopyrrolate, and a pharmaceutically acceptable liquid vehicle, optionally with additional pharmaceutically acceptable excipients. Other aspects of the invention relate to methods for making such compositions and methods of using such compositions for reversing the effects of non-depolarizing neuromuscular blocking agents. Preferably, the composition comprises neostigmine methylsulfate, glycopyrronium bromide, and a pharmaceutically acceptable liquid vehicle, and is provided in a pre-filled, ready-to-use sealed container, such as a pre-filled syringe, suitable for intravenous administration.

17 Claims, No Drawings

READY-TO-USE INJECTABLE PHARMACEUTICAL COMPOSITIONS COMPRISING NEOSTIGMINE AND GLYCOPYRROLATE

PRIORITY DATA

This application is a Continuation of copending application Ser. No. 16/170,948 filed on Oct. 25, 2018, which claims foreign priority to Indian Application No. 2018/41017552, filed on May 9, 2018, which is incorporated herein by reference in its entirety.

FIELD OF THE INVENTION

The present invention relates to stable, ready-to-use injectable compositions comprising the combination of neostigmine and glycopyrrolate, or their pharmaceutically acceptable salts, solvates, or hydrates, preferably where the finished dosage form is provided in a sealed container, e.g., an ampoule, vial and pre-filled syringe. These pharmaceutical compositions are suitable for subcutaneous, intravenous or intramuscular administration.

Aspects of the present invention further provide stable ready-to-use injectable compositions, comprising the combination of neostigmine, glycopyrrolate and a stabilizing amount of an aminopolycarboxylic acid. Other aspects of the invention relate to methods for making such compositions and methods of using such compositions. Preferably, the composition comprises neostigmine methylsulfate, glycopyrronium bromide, ethylenediaminetetraacetic acid (EDTA), and a pharmaceutically acceptable liquid vehicle, and the composition is useful in reversing the effects of non-depolarizing neuromuscular blocking agents.

BACKGROUND OF THE INVENTION

The present invention relates to stable, ready-to-use, injectable compositions, suitable for intravenous administration, comprising the combination of neostigmine and glycopyrrolate, or pharmaceutically acceptable salts, solvates, or hydrates thereof.

Neostigmine is a reversible acetylcholinesterase inhibitor, which blocks the breakdown of the neurotransmitter acetylcholine. Neostigmine has long been used by anesthesiologists to reverse the muscle paralysis artificially induced during surgical procedures. Examples of commercially-available neostigmine salts include chloride, bromide and methylsulfate salts. Neostigmine methylsulfate is represented by the following structural formula (I):

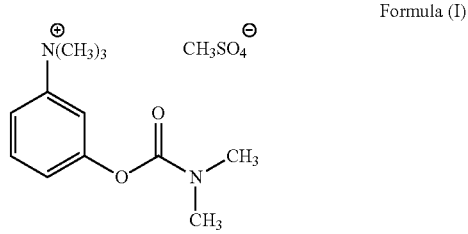

Formula (I)

Neostigmine methylsulfate is the active ingredient of a commercial product known as BLOXIVERZ®. BLOXIVERZ® solution for intravenous injection is indicated for the reversal of the effects of non-depolarizing neuromuscular blocking agents after surgery. BLOXIVERZ® is supplied as a sterile non-pyrogenic solution in a 10 mL multidose vial in 0.5 mg/mL and 1 mg/mL strengths. Each vial contains neostigmine methylsulfate, phenol, sodium acetate trihydrate and water for injection. The pH is adjusted, when necessary, with acetic acid/sodium hydroxide to achieve a value of 5.5

Glycopyrrolate is a quaternary ammonium salt with the following chemical name: 3-[(cyclopentylhydroxyphenylacetyl)oxy]-1,1-dimethyl pyrrolidinium bromide. Glycopyrrolate is an anti-cholinergic agent, which blocks neurotransmission by acetylcholine. Glycopyrrolate is used by anesthesiologists in the operating room setting or by other clinicians in clinical settings to counteract the cardiac side effects caused by neostigmine (e.g., bradycardia). Glycopyrronium bromide is represented by the following structural formula (II):

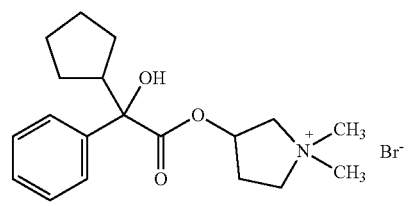

Formula (II)

Glycopyrronium bromide is the active ingredient of several commercial products such as CUVPOSA® oral solution, Lonhala Magnair kit inhalation solution, ROBINUL® injection and oral solution, ROBINUL FORTE® oral tablet and SEEBRI® powder for inhalation.

ROBINUL® solution for intramuscular or intravenous injection is indicated for use as a preoperative antimuscarinic to reduce salivary, tracheobronchial, and pharyngeal secretions; to reduce the volume and free acidity of gastric secretions; and to block cardiac vagal inhibitory reflexes during induction of anesthesia and intubation. ROBINUL® is supplied as a sterile non-pyrogenic solution in a single-use or multidose vial in 0.2 mg/mL strength. Each vial contains glycopyrrolate, water for injection, benzyl alcohol, hydrochloric acid and/or sodium hydroxide. The pH of the solution is about 2.0-3.0.

Glycopyrronium bromide and neostigmine methylsulfate are routinely administered simultaneously to reverse residual nondepolarizing (competitive) neuromuscular block. Numerous clinical studies, which demonstrate this to be a safe and effective combination have been published, e.g., R. K. Mirakhurm, et al., "*Glycopyrrolate—Neostigmine Mixture For Antagonism Of Neuromuscular Block: Comparison With Atropine—Mixture,*" British Journal of Anaesthesia, 49(8):825-829 (1977).

Developing injectable compositions comprising neostigmine and glycopyrrolate has always been a challenging task due to degradation of the active ingredients and subsequent impurity generation. Currently, glycopyrrolate and neostigmine injectable compositions are available in the form of glass ampoules and vials. Both the drugs are then filled into a syringe which is subsequently used for intravenous administration. The drugs are mixed in the syringe before administration to the patients. There is a high chance of dosage errors, due to erroneous handling while filling the syringe from ampoules or vials. Ampoules and vials made of glass are also difficult to handle.

Thus, there exists a need for the development of novel or improved compositions comprising neostigmine and glycopyrrolate that are stable and that minimize or prevent degradation. There is also a need to provide stable and ready-to-use injectable compositions comprising neostigmine and glycopyrrolate to improve patient compliance, reduce dosage errors, and reduce risk of contamination.

SUMMARY OF THE INVENTION

In one embodiment, the invention relates to stable, ready-to-use injectable pharmaceutical compositions comprising the combination of (i) neostigmine or a pharmaceutically acceptable salt, solvate or hydrate thereof, (ii) glycopyrrolate or a pharmaceutically acceptable salt, solvate or hydrate thereof, (iii) one or more aminopolycarboxylic acids; and (iv) a pharmaceutically acceptable liquid vehicle.

In certain embodiments, the compositions are provided in a sealed container selected from ampoules, vials and pre-filled syringes, preferably a sealed pre-filled syringe.

The pharmaceutical compositions according to the invention may be provided in the form of a solution, suspension, or emulsion.

In certain embodiments, the pharmaceutical compositions are suitable for subcutaneous, intravenous or intramuscular administration.

In a preferred embodiment, the pharmaceutical compositions comprise neostigmine methylsulfate and glycopyrronium bromide.

In a preferred embodiment, the one or more aminopolycarboxylic acids are selected from the group consisting of ethylenediaminetetraacetic acid (EDTA) and diethylenetriaminepentaacetic acid (DTPA). Most preferably, the aminopolycarboxylic acid is EDTA.

Certain embodiments relate to pharmaceutical compositions comprising (i) neostigmine or a pharmaceutically acceptable salt thereof, (ii) glycopyrrolate or a pharmaceutically acceptable salt thereof, (iii) a stabilizing amount of EDTA and (iv) a pharmaceutically acceptable liquid vehicle.

In certain embodiments, the compositions described herein will further comprise a pH adjusting agent. The pH adjusting agent is selected from the group consisting of sodium hydroxide, potassium hydroxide, magnesium hydroxide, sodium carbonate, Tris, sodium linoleate, sodium oleate, potassium carbonate, potassium linoleate, potassium oleate, hydrochloric acid and mixtures thereof.

In certain embodiments, the compositions described herein will further comprise a tonicity adjusting agent.

In certain embodiments, the compositions described herein will further comprise a preservative.

In another embodiment, the present invention relates to stable pharmaceutical compositions suitable for intravenous administration comprising neostigmine and glycopyrrolate, and one or more excipients selected from the group consisting of chelating agent, tonicity adjusting agent and antioxidant.

In one aspect, the present invention relates to stable ready-to-use injectable compositions suitable for intravenous administration comprising neostigmine methylsulfate, glycopyrronium bromide, ethylenediaminetetraacetic acid (EDTA) as a chelating agent, sodium citrate as an antioxidant, and a pharmaceutically acceptable liquid vehicle.

In another aspect, the present invention relates to stable ready-to-use injectable compositions suitable for intravenous administration comprising neostigmine, glycopyrrolate, ethylenediaminetetraacetic acid (EDTA) as a chelating agent, sodium chloride as a tonicity adjusting agent, sodium citrate as an antioxidant, and a pharmaceutically acceptable liquid vehicle.

In certain embodiments, the compositions described herein will have a pH ranging from about 3.0 to about 4.0, and preferably a pH from about 3.0 to about 3.5.

In certain embodiments, the compositions have a glycopyrrolate concentration from about 0.1 mg/mL to about 1 mg/mL, preferably from about 0.3 mg/mL to about 0.7 mg/mL, more preferably from about 0.2 mg/mL to about 0.7 mg/mL, more preferably about 0.5 mg/mL, and most preferably about 0.2 mg/mL.

In certain embodiments, the compositions have a neostigmine concentration from about 0.5 mg/mL to about 5 mg/mL, preferably from about 1 mg/mL to about 3 mg/mL, preferably about 2.5 mg/mL, and most preferably about 1 mg/mL.

In certain embodiments, the compositions have an aminopolycarboxylic acid concentration in the range from about 0.1 mg/mL to about 5 mg/mL of the composition, preferably in the range from about 0.5 mg/mL to about 2 mg/mL, and most preferably about 0.5 mg/mL.

In a preferred embodiment, the aminopolycarboxylic acid is EDTA, and the EDTA concentration is in the range from about 0.1 mg/mL to about 5 mg/mL of the composition, preferably in the range from about 0.5 mg/mL to about 2 mg/mL, and most preferably about 0.5 mg/mL.

In certain embodiments, the composition comprises from about 0.1 mg/mL to about 1 mg/mL of glycopyrrolate bromide; from about 0.5 mg/mL to about 5 mg/mL of neostigmine methylsulfate; and about 0.5 mg/mL of EDTA.

In certain embodiments, the composition comprises from about 0.2 mg/mL to about 0.7 mg/mL of glycopyrrolate bromide; from about 1 mg/mL to about 3 mg/mL of neostigmine methylsulfate; and about 0.5 mg/mL of EDTA.

In certain embodiments, the composition comprises about 2.5 mg/mL of neostigmine methylsulfate, about 0.5 mg/mL of glycopyrronium bromide and about 0.5 mg/mL of ethylenediaminetetraacetic acid (EDTA).

In certain embodiments, the composition comprises about 1.0 mg/mL of neostigmine methylsulfate, about 0.2 mg/mL of glycopyrronium bromide and about 0.5 mg/mL of ethylenediaminetetraacetic acid (EDTA).

In certain embodiments, the composition according to the invention is stable for at least 3 months at 25° C. and 60% relative humidity.

In certain embodiments, the composition according to the invention is stable for at least 3 months at 40° C. and 75% relative humidity.

In certain embodiments, the composition according to the invention is stable for at least 24 months when stored under room temperature.

In certain embodiments, the composition according to the invention has a level of Glycopyrrolate Impurity C that is less than 1% as measured by HPLC, preferably less than 0.5% as measured by HPLC, and most preferably less than 0.25% as measured by HPLC.

In certain embodiments, the compositions according to the invention are used in methods of treatment, which comprise administering the composition to a patient in need thereof, in order to reverse the effects of non-depolarizing neuromuscular blocking agents.

In certain embodiments, the invention relates to methods for making a composition, which comprise (i) dispensing water for injection; (ii) adding one or more aminopolycarboxylic acids to form a first solution; (iii) adding glycopyrrolate and neostigmine to the first solution to form a second solution; and (iv) optionally, adjusting the pH of the second solution by adding a suitable acid or base, e.g., hydrochloric acid and/or sodium hydroxide.

In certain embodiments, the invention relates to methods for making a composition, which comprise (i) dispensing water for injection; (ii) adding sodium chloride, EDTA and a pH adjusting agent to the water for injection to form a first solution; (iii) adding glycopyrrolate and neostigmine to the first solution to form a second solution; (iv) adding an antioxidant to the second solution to form a third solution; and (v) optionally, adjusting the pH of the third solution by adding a suitable acid or base, e.g., hydrochloric acid and/or sodium hydroxide.

In certain embodiments, these methods for making the compositions of the invention will further comprise filling the solution into vials; and sealing the vials. For example, rubber stoppers may be used for sealing the vials. Certain embodiments additionally relate to sterilizing the finished products, e.g., filtration through a bacterial-retaining filter, aseptic filling, terminal sterilization, incorporation of sterilizing agents, irradiation, and/or heating.

DETAILED DESCRIPTION OF THE INVENTION

As used herein, the terms "neostigmine" and "glycopyrrolate" comprise all isomers, enantiomers, diastereomers, pharmaceutically acceptable salts, solvates, prodrugs, complexes, or hydrates thereof, as well as any polymorphic or amorphous forms or combinations thereof. The terms "neostigmine" and "glycopyrrolate" also refer to the corresponding free base or free acid forms. Preferred salt forms include neostigmine methylsulfate and glycopyrronium bromide.

Within the context of the present invention, the term "ready-to-use" or "RTU" as used herein refers to an injectable composition that is stable and is not reconstituted from a lyophilizate. The term "RTU" also encompasses within its scope, injectable compositions that are stable and must be diluted from a concentrated, liquid solution just prior to use.

The injectable composition of the present invention provides a ready-to-use injectable composition, whereby there is no requirement for reconstituting the composition prior to its administration, thus eliminating the tedious task of reconstitution, especially in an aseptic area. As such, the compositions of the present invention provide a convenient dosage form, improve patient compliance, reduce dosage errors, and reduce risk of contamination.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent.

For purposes of the present invention, "stabilizing amount" shall be understood to include those amounts which increase or enhance the stability of the neostigmine and glycopyrrolate in the compositions described herein, as compared to a composition without the stabilizing agent.

The term "stable" refers to both the physical and chemical stability of a composition in any form, such as a solution. A composition is said to be stable if it exhibits minimal change over time relative to when it is manufactured. Stability is measured at various time points through a planned product expiration date with evaluation criteria including such items as therapeutic activity, appearance, levels of particulate matter, pH, content of active ingredient(s), and levels of degradation products, impurities, or related substances.

According to present invention, the composition of the present invention is in a form selected from solution, suspension, or emulsion suitable for parenteral administration comprising neostigmine and glycopyrrolate or their pharmaceutically acceptable salts thereof with one or more parenterally acceptable excipients.

It is preferred that compositions of the present invention are provided in a ready-to-use solution. The compositions of the invention can be administered in any conventional manner. It will be readily appreciated by those skilled in the art how to administer compositions of the present invention to a human or an animal.

An embodiment of the present invention comprises neostigmine methylsulfate in an amount from about 0.5 mg/mL to about 5 mg/mL, preferably about 1 mg/mL to about 3 mg/mL, more preferably 2.5 mg/mL, and most preferably about 1 mg/mL.

An embodiment of the present invention comprises glycopyrronium bromide in an amount from about 0.1 mg/mL to about 1 mg/mL, preferably from about 0.2 mg/mL to about 0.7 mg/mL, more preferably about 0.5 mg/mL, and most preferably about 0.2 mg/mL.

As used herein, "chelating agent" refers to an agent which forms via two or more of its functional groups stable complexes with metal cations, e.g., preferably a polyacetic acid or a pharmaceutically acceptable salt thereof like EDTA and DTPA. Chelating agents are capable of forming more than one bond. Ethylene diamine, for example, is bidentate (two links), tripyridyl is tridentate (three) and ethylene diamine tetra acetic acid (EDTA) is hexadentate (six) which makes it particularly effective as a pharmaceutical chelating agent. One of the consequences of chelation typically is the formation of a cyclic structure, which may have high thermodynamic and thermal stability.

The amount of chelating agent may range from about 0.01 mg/mL to about 5 mg/mL of the composition, preferably from about 0.5 mg/mL to about 2 mg/mL, and most preferably about 0.5 mg/mL.

Preferably the chelating agent is a bivalent cation chelator and more preferably, the chelator is selected from the group consisting of ethylenediaminetetraacetic acid (EDTA), diethylenetriaminepentaacetic acid (DTPA), ethylene glycol-bis (β-aminoethyl ether)-tetra acetic acid (EGTA), N-(hydroxyethyl) ethylenediaminetriacetic acid (HEDTA), nitrilotriacetic acid (NTA), triethanolamine, 8-hydroxyquinoline, tartaric acid, phosphoric acid, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. More preferably, the chelating agent is selected from the group consisting of EDTA, DTPA, tartaric acid, phosphoric acid, gluconic acid or a pharmaceutically acceptable salt thereof.

In a preferred embodiment, the chelating agent is an aminopolycarboxylic acid, i.e., a compound containing one or more nitrogen atoms connected through carbon atoms to two or more carboxylic acid groups. Examples of aminopolycarboxylic acids include EDTA and DTPA, or pharmaceutically acceptable salts thereof. The amount of aminopolycarboxylic acid may range from about 0.1 mg/mL to about 5 mg/mL of the composition, preferably from about 0.5 mg/mL to about 2 mg/mL, and most preferably about 0.5 mg/mL.

As used herein, "antioxidant" refers to an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and others known to those of ordinary skill in the art. The amount of antioxidant may range from about 0.1 mg/mL to about 50 mg/mL of the composition, and preferably from about 0.5 mg/mL to about 25 mg/mL.

The pharmaceutical compositions of the present invention may also contain pH adjusting agents or neutralizing agents. The pH adjusting agent or neutralizing agents is selected from the group consisting of sodium hydroxide, potassium hydroxide, magnesium hydroxide, sodium carbonate, Tris, sodium linoleate, sodium oleate, potassium carbonate, potassium linoleate, potassium oleate, hydrochloric acid and mixtures thereof. The pH of the compositions usually ranges from about 2.0 to about 5.0. More preferably the pH of the compositions usually ranges from about 3.0 to about 4.0 and preferably the pH of the compositions ranges from about 3.0 to about 3.5.

The pharmaceutical compositions may optionally contain buffering agent, which is used to resist change in pH upon dilution or addition of acid or alkali. Such compounds include, by way of example and without limitation, acetic acid, sodium acetate, adipic acid, benzoic acid, sodium benzoate, maleic acid, monobasic sodium phosphate, dibasic sodium phosphate, disodium hydrogen phosphate dodecahydrate, lactic acid, tartaric acid, potassium metaphosphate, potassium phosphate, monobasic sodium acetate, sodium bicarbonate, sodium tartrate and others known to those of ordinary skill in the art.

The pharmaceutical compositions may contain a "tonicity modifier" that can be used to adjust the tonicity of the liquid formulation. Suitable tonicity modifiers include glycerine, lactose, mannitol, dextrose, sodium chloride, sodium sulphate, sorbitol, trehalose and others known to those or ordinary skill in the art. In one embodiment, the tonicity of the liquid formulation approximates that of the tonicity of blood or plasma. The amount of tonicity modifier may range from about 1 mg/mL to about 20 mg/mL of the composition, preferable from about 5-10 mg/mL.

The present invention provides for a composition that may optionally comprise one or more preservatives. The term "preservative" refers to a substance present in a composition which can, at least in part, prevent and/or reduce decomposition of the composition. In some embodiments, the preservative may prevent and/or reduce decomposition of the composition by microbial growth in the composition. Preferably, the preservative is pharmaceutically acceptable.

In some embodiments, the preservative may be present in the composition at a concentration that allows for a multi-dose formulation of the composition. In some embodiments, the preservative may be present in the composition at a concentration that prevents and/or reduces decomposition of unused portions of the composition in a multi-dose formulation. In some embodiments, the preservative may allow for up to about 14 days of use, preferably up to about 30 days of use, more preferably up to about 60 days of use, and most preferably up to about 90 days of use of a multi-dose formulation of the composition.

In some embodiments, the preservative may be present in the composition at a concentration of in the range of about 1 to 10 mg/mL, preferably in the range of about 3 and 7 mg/mL, more preferably in the range of about 4 and 5 mg/mL, more preferably at about 4.5 mg/mL.

Preferably, preservatives comprise one or more of benzalkonium chloride, benzethonium chloride, benzoic acid, benzyl alcohol, benzyl paraben, bronopol, butyl paraben, cetrimide, cetylpyridinium chloride, chlorbutanol, chlorhexidine, chlorocresol, chloroxylenol, cresol, ethyl alcohol, ethyl paraben, ethylparaben, glycerin, hexetidine, imidurea, isobutyl paraben, meta-cresol, methyl paraben, methylparaben, phenol, phenoxyethanol, phenylethyl alcohol, phenylmercuric nitrate, p-hydroxybenzoic acid esters, polyhexamethylene biguanide ("PHMB"), potassium sorbate, propyl paraben, propylene glycol, sodium benzoate, sodium perborate, sodium propionate, sorbic acid, stabilized thimerosal, and/or thimerosal. Preferably, the preservative comprises phenol.

The pharmaceutical compositions may optionally contain a stabilizing agent, which is a compound used to stabilize a therapeutic agent against physical, chemical, or biochemical process that would otherwise reduce the therapeutic activity of the agent. Suitable stabilizers include, by way of example and without limitation, albumin, sialic acid, creatinine, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

The pharmaceutical compositions described herein may be in any form suitable for injection. To prepare such compositions, active drug(s) are dissolved or suspended in a parenterally acceptable liquid vehicle. Illustrative vehicles and solvents include, but are not limited to, water, alcohols, glycols, dimethylacetamide N-methylpyrollidone, dimethyl sulfoxide, Ringers solution, and isotonic sodium chloride solution.

The formulations of the present invention may be sterilized. Non-limiting examples of sterilization techniques include filtration through a bacterial-retaining filter, terminal sterilization, incorporation of sterilizing agents, irradiation, and heating.

Sterilization may be accomplished by any of the conventional methods including aseptic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A pharmaceutically inert gas may be bubbled into the solution to drive out oxygen, which may be selected from nitrogen or carbon dioxide.

Containers suitable according to the present invention are those known in the art. They include vials, pre-filled syringes, infusion bags, bottles and ampoule presentations. Containers may be fabricated from glass or from polymeric materials. Suitable containers should be of a size sufficient to hold one or more doses of neostigmine and glycopyrrolate.

The present invention provides for compositions in single-dose and/or multi-dose formulations. In some embodiments, the composition may be contained in vials. In some embodiments, the vials may comprise clear glass, amber glass, or plastic. In some embodiments, the vials may be in the range of about 0.1 to 500 mL in volume, preferably in the range of about 0.5 to 250 mL, more preferably in the range of about 1 to 100 mL, and most preferably in the range of about 10 to 50 mL. In some embodiments, the composition may exist in a 5 mL vial. In some embodiments, the 5 mL vial may be a single-dose formulation. In some embodiments, the 10 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days. In some embodiments, the composition may be lyophilized.

The polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition, crystal zenith (CZ) resin containers and similar resins can be used as rigid containers and syringes.

A ready-to-use pre-filled syringe comprising sterile and stable glycopyrrolate-neostigmine compositions according to the invention will be advantageous, as compared to the individual compositions. Being pre-filled, there is no requirement to mix the drugs prior to administration, thereby reducing contamination issues. A pre-filled syringe fabricated from a polymer will not only be convenient for handling, storage and administration, but will also minimize mixing or dosing errors.

The pre-filled syringe according to the invention includes single use auto injectors and reusable auto injectors.

The compositions of the invention are preferably used to reverse the effects of non-depolarizing neuromuscular blocking agents (NMBAs) in a patient in need thereof. The skilled artisan may use any conventional method for administration of glycopyrronium bromide and neostigmine methylsulfate, to reverse residual nondepolarizing (competitive) neuromuscular block.

The following examples are provided for illustrative purpose only and should not be considered as limiting the scope of present invention in any way.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

General HPLC Procedure

As explained in detail below, the following HPLC procedure can be used to detect and quantify impurities of neostigmine and glycopyrrolate. The materials and general conditions are listed below:

TABLE 1

Chromatographic conditions

| | |
|---|---|
| Chromatographic Mode | Gradient |
| Column | Symmetry C18 - 5 μm, 4.6 mm × 150 mm [Part No.: WAT045905] |
| Wavelength | 222 nm |
| Flow rate | 1.0 mL/min |
| Injection volume | 50 μL |
| Column temperature | 40° C. |
| Sample temperature | 25° C. |
| Retention time | About 4 minutes for Neostigmine methylsulfate peak and about 34 minutes for glycopyrronium bromide peak. |
| Run time | 70 minutes |
| Needle Wash | Mixture of Water: Methanol in the ratio of 20:80 v/v respectively |
| Mobile Phase A | Prepare a mixture of a buffer having a pH of 2.50 ± 0.05, comprising acetonitrile and methanol in the |
| Mobile Phase B | Prepare a mixture of Buffer pH 2.50 ± 0.05, acetonitrile and methanol in the ratio of 35:50:15 |

TABLE 2

Gradient Programme

| Time (min) | % Mobile Phase A | % Mobile Phase B |
|---|---|---|
| 0.0 | 100 | 0 |
| 20.0 | 100 | 0 |
| 40.0 | 25 | 75 |
| 50.0 | 25 | 75 |
| 55.0 | 10 | 90 |
| 60.0 | 10 | 90 |
| 62.0 | 100 | 0 |
| 70.0 | 100 | 0 |

The relative retention times (RRTs), relative response factor (RRF) of the impurities with respect to Neostigmine and Glycopyrronium bromide peaks are shown in the Table 3 below.

TABLE 3

RRT and RRF for Neostigmine and Glycopyrronium Impurities

| S. No. | Name of Impurity | Structure | RRT* | RRF* |
|---|---|---|---|---|
| 1 | Neostigmine Impurity A (3-Hydroxy-N,N,N-trimethylanilinum methyl sulfate) | 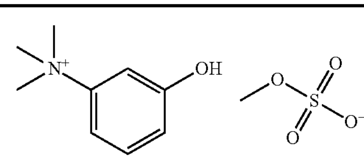 | 0.66 | 2.20 |

TABLE 3-continued

RRT and RRF for Neostigmine and Glycopyrronium Impurities

| S. No. | Name of Impurity | Structure | RRT* | RRF* |
|---|---|---|---|---|
| 2 | Neostigmine Impurity B (3-(Dimethyl amino)phenol) | 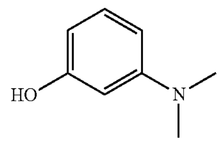 | 0.85 | 4.44 |
| 3 | Neostigmine Impurity C 3-(dimethylamino)phenyl dimethyl carbamate | 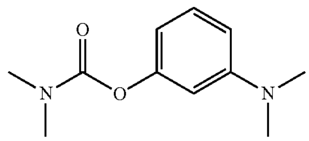 | 5.32 | 1.54 |
| 4 | Didehydro glycopyrrolate 3-[2-(cyclopent-1-en-1-yl)-2-hydroxy-2-phenylacetoxy]-1,1-dimethylpyrrolidin-1-ium bromide | 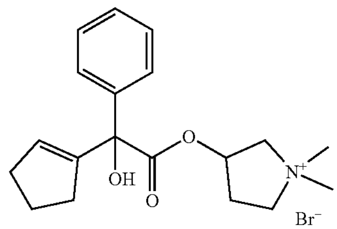 [SMILES: C[N+]1(C)CCC(OC(=O)C(O)(C2=CCCC2)c2ccccc2)C1 ; [Br-]] | 0.94 | 0.93 |
| 5 | Glycopyrrolate impurity B 3-[(cyclopentyl-hydroxyphenylacetyl)oxy]-1-methyl pyrrolidine | 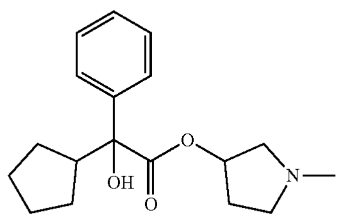 [SMILES: CN1CCC(OC(=O)C(O)(c2ccccc2)C2CCCC2)C1] | 1.01 | 1.23 |
| 6 | Glycopyrrolate impurity C (2RS)-2-cyclopentyl-2-hydroxy-2-phenylacetic acid | 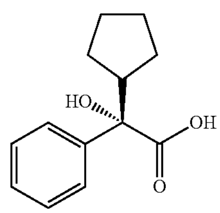 [SMILES: O=C(O)[C@@](O)(c1ccccc1)C1CCCC1] | 1.13 | 1.61 |
| 7 | Glycopyrrolate impurity I (3RS)-3-[(2SR)-(2-(4-chlorophenyl)-2-cyclopentyl-2 hydroxyacetyl)oxy]-1,1-dimethylpyrrolidinium) | 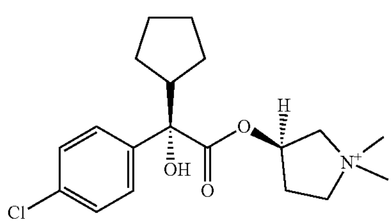 | 1.09 | 2.04 |
| 8 | Glycopyrrolate impurity L Methyl-(2RS)-2-cyclopentyl-2-hydroxy-2-phenylacetate | 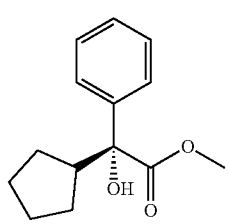 [SMILES: COC(=O)[C@](O)(c1ccccc1)C1CCCC1] | 1.20 | 1.12 |

Notes:
RRT with respect to Neostigmine peak for S. No. 1-3 and RRT with respect to glycopyrronium peak for S. No. 4-8.

Reference Example 1

The following reference example was prepared in a conventional manner:

TABLE 4

| No. | Ingredient | Unit Qty (mg/mL) |
|---|---|---|
| 1 | Glycopyrrolate | 0.5 |
| 2 | Neostigmine methylsulfate | 2.5 |
| 3 | Disodium hydrogen phosphate dodecahydrate | 23.0 |
| 4 | Citric acid monohydrate | 15.00 |
| 5 | Citric acid solution | q. s |
| 6 | Water for injection | — |
|  | Total | 1 mL |

Manufacturing Procedure:

1. 70% of the total quantity of the water for injection was dispensed.
2. Disodium hydrogen phosphate dodecahydrate and citric acid monohydrate were added to the water for injection to form a solution.
3. Glycopyrrolate and Neostigmine were then added to the above solution.
4. The pH of the resulting solution was adjusted to 3.2, using a pH adjusting agent (i.e., citric acid solution).
5. The volume was adjusted to 1500 mL with the remaining water for injection.
6. The solution was filled into 2 mL vials, and the vials were sealed using rubber stoppers.
7. The vials were terminally sterilized by autoclaving.

Using the General HPLC methods described above, the reference example was tested (i) initially, (ii) at three months at 25° C. and 60% relative humidity, and (iii) at three months at 40° C. and 75% relative humidity. The amount of related substances for glycopyrrolate and neostigmine are reported below as percentages (%) according to HPLC.

TABLE 5

Stability Data for Reference Example

| Reference Example | Initial | 3 Months at 25° C./60% RH | 3 Months at 40° C./75% RH |
|---|---|---|---|
| Related Substances for Glycopyrrolate | | | |
| Didehydro Glycopyrrolate | 0.03 | ND | ND |
| Glycopyrrolate Impurity B | ND | ND | ND |
| Glycopyrrolate Impurity C | 0.22 | 0.36 | 1.05 |
| Glycopyrrolate Impurity I | ND | ND | ND |
| Glycopyrrolate Impurity L | ND | ND | ND |
| Highest unknown impurity | 0.11 | 0.11 | 0.11 |
| Total Impurities | 0.41 | 0.56 | 1.25 |
| Related Substances for Neostigmine | | | |
| Neostigmine Impurity A | 0.03 | 0.06 | 0.16 |
| Neostigmine Impurity B | ND | ND | ND |
| Neostigmine Impurity C | ND | ND | ND |
| Highest unknown impurity | 0.04 | 0.09 | 0.08 |
| Total Impurities | 0.13 | 0.24 | 0.31 |

Example 1

TABLE 6

Compositions of neostigmine methylsulfate and glycopyrrolate (2.5 mg/mL; 0.5 mg/mL)

| S. No. | Ingredient Name | I | II | III | IV | V | VI | VII |
|---|---|---|---|---|---|---|---|---|
|  |  | Unit Qty (mg/mL) | | | | | | |
| 1 | Glycopyrrolate | 0.5 | 0.5 | 0.5 | 0.5 | 0.5 | 0.5 | 0.5 |
| 2 | Neostigmine methylsulfate | 2.5 | 2.5 | 2.5 | 2.5 | 2.5 | 2.5 | 2.5 |
| 3 | EDTA | 0.5 | 0.5 | 0.5 | 0.5 | 0.5 | 0.5 | 0.5 |
| 4 | L-Cysteine HCl | — | 7.0 | — | — | — | — | — |
| 5 | L-Methionine | — | — | 25.0 | — | — | — | — |
| 6 | Sodium metabisulfite | — | — | — | 1.8 | — | — | — |
| 7 | Sodium citrate dihydrate | — | — | — | — | 8.3 | — | — |
| 8 | Mono-thioglycerol | — | — | — | — | — | 5.0 | — |
| 9 | Disodium hydrogen phosphate dodecahydrate | — | — | — | — | — | — | 23.0 |
| 10 | Citric acid monohydrate | — | — | — | — | — | — | 15.00 |
| 11 | Citric acid solution | — | — | — | — | — | — | q.s |
| 12 | Sodium chloride | 8.0 | 8.0 | 8.0 | 8.0 | 8.0 | 8.0 | — |
| 13 | Hydrochloric acid* | q.s | q.s | q.s | q.s | q.s | q.s | — |
| 14 | Sodium hydroxide* | q.s | q.s | q.s | q.s | q.s | q.s | — |
| 15 | Water for injection | q.s | q.s | q.s | q.s | q.s | q.s | — |
|  | Total | 1 mL | 1 mL | 1 mL | 1 mL | 1 mL | 1 mL | 1 mL |

Manufacturing Procedure:

1. 70% of the total quantity of the water for injection was dispensed.
2. Sodium chloride, EDTA and optionally, an anti-oxidant and a pH adjusting agent, were added to the water for injection to form a solution.
3. Glycopyrrolate and Neostigmine were then added to the above solution.
4. pH was adjusted to 3.2 by using a suitable amount of a pH adjusting agent (e.g., 0.1N HCl solution to decrease pH to 3.2 or 0.1M sodium hydroxide solution to increase pH to 3.2)
5. The volume was adjusted to 300 mL with the remaining water for injection.
6. The solution was filled into 2 mL vials and the vials were sealed using rubber stoppers.
7. The vials were terminally sterilized by autoclaving.

Using the General HPLC methods described above, the compositions of Example 1 were tested (i) initially, (ii) at three months at 25° C. and 60% relative humidity, and (iii) at three months at 40° C. and 75% relative humidity. The amount of related substances for glycopyrrolate and neostigmine are reported below in Table 7, as percentages (%) according to HPLC.

TABLE 7

Stability Data for compositions of neostigmine methylsulfate and glycopyrrolate (2.5 mg/mL; 0.5 mg/mL)

| | \multicolumn{7}{c}{Composition} | | | | | | |
|---|---|---|---|---|---|---|---|
| | I | II | III | IV | V | VI | VII |

Initial:
Related Substances for Glycopyrrolate

| | I | II | III | IV | V | VI | VII |
|---|---|---|---|---|---|---|---|
| Didehydro Glycopyrrolate | 0.01 | 0.02 | 0.01 | 0.01 | ND | ND | ND |
| Glycopyrrolate Impurity B | ND | ND | ND | ND | ND | ND | ND |
| Glycopyrrolate Impurity C | 0.12 | 0.13 | 0.08 | 0.14 | 0.07 | 0.09 | 0.16 |
| Glycopyrrolate Impurity I | ND | ND | ND | ND | ND | ND | ND |
| Glycopyrrolate Impurity L | ND | ND | ND | ND | ND | ND | ND |
| Highest unknown impurity | 0.11 | 0.11 | 0.11 | 0.11 | 0.11 | 0.1 | 0.11 |
| Total Impurities | 0.39 | 0.52 | 0.32 | 0.41 | 0.39 | 0.44 | 0.43 |

Related Substances for Neostigmine

| | I | II | III | IV | V | VI | VII |
|---|---|---|---|---|---|---|---|
| Neostigmine Impurity A | 0.02 | 0.05 | ND | 0.6 | 0.03 | 0.03 | 0.05 |
| Neostigmine Impurity B | ND | ND | ND | 0 | ND | ND | ND |
| Neostigmine Impurity C | ND | ND | ND | ND | ND | ND | ND |
| Highest unknown impurity | 0.05 | 0.04 | 0.12 | 0.65 | 0.05 | 0.04 | 0.08 |
| Total Impurities | 0.16 | 0.17 | 0.25 | 2.01 | 0.16 | 0.09 | 0.21 |

3 Months at 25° C./60% RH:
Related Substances for Glycopyrrolate

| | I | II | III | IV | V | VI | VII |
|---|---|---|---|---|---|---|---|
| Didehydro Glycopyrrolate | ND | ND | 0.03 | 0.02 | ND | ND | ND |
| Glycopyrrolate Impurity B | ND | ND | ND | ND | ND | ND | ND |
| Glycopyrrolate Impurity C | 0.13 | 0.15 | 0.12 | 0.29 | 0.11 | 0.1 | 0.32 |
| Glycopyrrolate Impurity I | ND | ND | ND | ND | ND | ND | ND |
| Glycopyrrolate Impurity L | ND | ND | ND | ND | ND | ND | ND |
| Highest unknown impurity | 0.11 | 0.11 | 0.1 | 0.08 | 0.09 | 0.09 | 0.08 |
| Total Impurities | 0.32 | 0.26 | 0.26 | 0.41 | 0.29 | 0.22 | 0.46 |

Related Substances for Neostigmine

| | I | II | III | IV | V | VI | VII |
|---|---|---|---|---|---|---|---|
| Neostigmine Impurity A | 0.04 | 0.18 | 0.06 | 1.41 | 0.06 | 0.22 | 0.09 |
| Neostigmine Impurity B | ND | ND | ND | ND | ND | ND | ND |
| Neostigmine Impurity C | ND | ND | ND | ND | ND | ND | ND |
| Highest unknown impurity | 0.08 | 0.23 | 0.14 | 1.44 | 0.06 | 0.22 | 0.08 |
| Total Impurities | 0.2 | 0.99 | 0.37 | 3.37 | 0.20 | 1.06 | 0.3 |

3 Months at 40° C./60% RH:
Related Substances for Glycopyrrolate

| | I | II | III | IV | V | VI | VII |
|---|---|---|---|---|---|---|---|
| Didehydro Glycopyrrolate | ND | ND | 0.04 | 0.02 | ND | 0.01 | ND |
| Glycopyrrolate Impurity B | ND | ND | ND | ND | ND | ND | ND |
| Glycopyrrolate Impurity C | 0.34 | 0.35 | 0.38 | 0.84 | 0.4 | 0.29 | 1.04 |
| Glycopyrrolate Impurity I | ND | ND | ND | ND | ND | ND | ND |
| Glycopyrrolate Impurity L | ND | ND | ND | ND | ND | ND | ND |
| Highest unknown impurity | 0.11 | 0.11 | 0.11 | 0.11 | 0.12 | 0.1 | 0.11 |
| Total Impurities | 0.52 | 0.48 | 0.66 | 0.98 | 0.6 | 0.4 | 1.22 |

Related Substances for Neostigmine

| | I | II | III | IV | V | VI | VII |
|---|---|---|---|---|---|---|---|
| Neostigmine Impurity A | 0.1 | 0.34 | 0.17 | 2.42 | 0.17 | 0.51 | 0.26 |
| Neostigmine Impurity B | ND | ND | ND | ND | ND | ND | ND |
| Neostigmine Impurity C | ND | 0.05 | 0.02 | 0.03 | ND | ND | ND |
| Highest unknown impurity | 0.08 | 0.18 | 0.7 | 1.77 | 0.07 | 0.33 | 0.08 |
| Total Impurities | 0.27 | 1.02 | 1.1 | 4.86 | 0.32 | 1.76 | 0.41 |

The stability data generated above by subjecting ready-to-use vials to accelerated and room temperature stability for 3 months indicated that neostigmine-glycopyrrolate compositions comprising ethylenediametetraacetic acid (EDTA) displayed improved stability when compared to the neostigmine-glycopyrrolate reference example.

Example 2

TABLE 8

Compositions of neostigmine methylsulfate and glycopyrrolate (1 mg/mL; 0.2 mg/mL)

| | VIII | IX |
|---|---|---|
| Ingredients | \multicolumn{2}{c}{mg/mL} | |
| Neostigmine Methylsulfate | 1.0 mg | 1.0 mg |
| Glycopyrrolate | 0.2 mg | 0.2 mg |
| Phenol | — | 4.5 mg |
| EDTA | 0.5 mg | 0.5 mg |
| Sodium chloride | 8 mg | 8 mg |
| Hydrochloric acid | q.s to adjust pH | q.s to adjust pH |
| Sodium Hydroxide | q.s to adjust pH | q.s to adjust pH |
| Water for Injection | q.s. to 1 mL | q.s. to 1 mL |

Manufacturing Procedure:
Composition VIII in Pre-Filled Syringe & Single-Dose Vial
1. 70% water for injection was dispensed.
2. Sodium chloride, EDTA and optionally, a pH adjusting agent, were added to the water for injection to form a solution.
3. Glycopyrrolate and Neostigmine were then added to the above solution.
4. The pH was adjusted to 3.2 by using a suitable amount of a pH adjusting agent (e.g., 0.1N HCl solution to decrease pH to 3.2 or 0.1M sodium hydroxide solution to increase pH to 3.2).
5. The volume was adjusted to 500 mL with the remaining water for injection.
6. The solution was filled into 5 mL vials/pre-filled syringes and stoppered using rubber stopper.
7. 5 ml vials/pre-filled syringes were terminally sterilized by autoclaving.

Composition IX in Multi-Dose Vial:
1. 70% water for injection was dispensed.
2. Sodium chloride, EDTA, phenol and a pH adjusting agent, were added to the water for injection to form a solution.
3. Glycopyrrolate and Neostigmine were then added to the above solution.
4. The pH was adjusted to 3.2 by using a suitable amount of a pH adjusting agent (e.g., 0.1N HCl solution to decrease pH to 3.2 or 0.1M sodium hydroxide solution to increase pH to 3.2)
5. The volume was adjusted to 500 mL with the remaining water for injection.
6. The solution was filled in 10 mL multi-dose vials and stoppered using rubber stopper.
7. The vials were terminally sterilized by autoclaving.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:
1. A ready-to-use injectable pharmaceutical composition comprising:
   (i) about 0.5 mg/mL of neostigmine or a pharmaceutically acceptable salt, solvate or hydrate thereof;
   (ii) about 0.1 mg/mL of glycopyrrolate or a pharmaceutically acceptable salt, solvate or hydrate thereof;
   and (iii) a pharmaceutically acceptable liquid vehicle, wherein a level of Glycopyrrolate Impurity C in the composition is less than 1% when stored at 40° C. and 75% relative humidity for at least 3 months wherein the composition has a pH ranging from about 3.0 to about 4.0.

2. The pharmaceutical composition according to claim 1, comprising neostigmine methylsulfate and glycopyrronium bromide.

3. The pharmaceutical composition according to claim 1, wherein the composition is provided in a sealed container selected from the group consisting of a vial and a pre-filled syringe.

4. The pharmaceutical composition according to claim 1, wherein the composition is provided in a clear glass vial, an amber glass vial, a plastic vial or a pre-filled syringe.

5. The pharmaceutical composition according to claim 1, wherein the composition is in the form of a solution.

6. The pharmaceutical composition according to claim 1, wherein the composition is suitable for subcutaneous, intravenous or intramuscular administration.

7. The pharmaceutical composition according to claim 1, wherein the composition has a pH ranging from about 3.0 to about 3.5.

8. The pharmaceutical composition according to claim 1, further comprising a tonicity modifier.

9. The pharmaceutical composition according to claim 8, wherein the tonicity modifier is selected from the group consisting of glycerine, lactose, mannitol, dextrose, sodium chloride, sodium sulphate, sorbitol, and trehalose.

10. The pharmaceutical composition according to claim 8, wherein the tonicity modifier is present in an amount from about 1 mg/mL to about 20 mg/mL of the composition.

11. The pharmaceutical composition according to claim 8, wherein the tonicity modifier is present in an amount from about 5-10 mg/mL.

12. The pharmaceutical composition according to claim 1, which is stable for at least 3 months at 25° C. and 60% relative humidity.

13. The pharmaceutical composition of claim 1, wherein the level of Glycopyrrolate Impurity C is less than 1% (w/w) as measured by HPLC.

14. The pharmaceutical composition of claim 1, wherein the composition is sterilized.

15. The pharmaceutical composition of claim 1, wherein the composition is sterilized using a technique selected from the group consisting of filtration through a bacterial-retaining filter, terminal sterilization, incorporation of sterilizing agents, irradiation, and heating.

16. The pharmaceutical composition of claim 1, wherein the composition is sterilized using a technique selected from the group consisting of aseptic filling, irradiation and heat sterilization.

17. A method for treating a neuromuscular disease, comprising administering the pharmaceutical composition according to claim 1 to a patient in need thereof.

* * * * *